United States Patent [19]

Papa et al.

[11] Patent Number: 5,231,222
[45] Date of Patent: Jul. 27, 1993

[54] ESTERIFICATION PROCESS

[75] Inventors: Anthony J. Papa, St. Albans; David R. Bryant, South Charleston, both of W. Va.

[73] Assignee: Union Carbide Chemicals & Plastics Technology Corporation, Danbury, Conn.

[21] Appl. No.: 724,811

[22] Filed: Jul. 2, 1991

[51] Int. Cl.$^5$ .......................................... C07C 67/08
[52] U.S. Cl. ..................................... 560/265; 560/205
[58] Field of Search ................... 560/205, 265; 562/91

[56] References Cited

U.S. PATENT DOCUMENTS

| | | | |
|---|---|---|---|
| 3,071,604 | 1/1963 | Bloomfield et al. | 260/410.6 |
| 3,692,822 | 9/1972 | Hay et al. | 560/265 |
| 4,698,440 | 10/1987 | Blair et al. | 560/205 |

FOREIGN PATENT DOCUMENTS

| | | |
|---|---|---|
| 138788 | 4/1970 | Czechoslovakia . |
| 1193282 | 9/1985 | Canada ............................ 560/205 |
| 009886 | 4/1980 | European Pat. Off. . |
| 0158499 | 10/1985 | European Pat. Off. . |
| 1173089 | 12/1969 | United Kingdom . |
| 1262645 | 2/1972 | United Kingdom . |

OTHER PUBLICATIONS

"Effect of Catalysts on the Esterification of Stearic Acid" by V. Peterka in *Prumysl Potravin*, vol. 27, No. 2, pp. 115-116, (1976) (English Translation).
"Studies of the Rate of Oleic Acid Esterification with Methanol" by A. Cybulski in *Chemica Stosowana*, vol. 26, No. 1, pp. 85-97, (1982), Institute of Chem. Warsaw (English Translation).
Chapter 8 of "Sulphonation and Related Reactions" by E. E. Gilbert, Interscience Pub., (1965) pp. 425-431.
"Esterification of Butanol and Acetic Acid" by C. E. Leyes and D. F. Othmer, *Ind. Eng. Chem.*, vol. 37, pp. 968-977 (1945).
"Cause of the Slowdown of the Esterification Reaction Catalyzed by Aromatic Sulfonic Acids," B. I. Charelishvili et al in *Kinetika i Kataliz*, vol. 19. No. 4, pp. 899-903 (1977); English Translation, pp. 715-718 (1978).

*Primary Examiner*—José G. Dees
*Assistant Examiner*—B. Frazier
*Attorney, Agent, or Firm*—R. J. Finnegan

[57] ABSTRACT

An improved esterification process for producing volatile product esters by reacting a lower linear hydrocarbyl carboxylic acid with an alcohol containing from 2 to 10 carbon atoms, in a substantially non-aqueous medium, the improvement comprising minimizing the amount of acidic sulfate contained in the product ester by employing as the esterification catalyst a long chain alkylbenzene sulfonic acid catalyst, the alkyl radical containing from 8 to 20 carbon atoms, or mixtures of such catalysts.

22 Claims, 1 Drawing Sheet

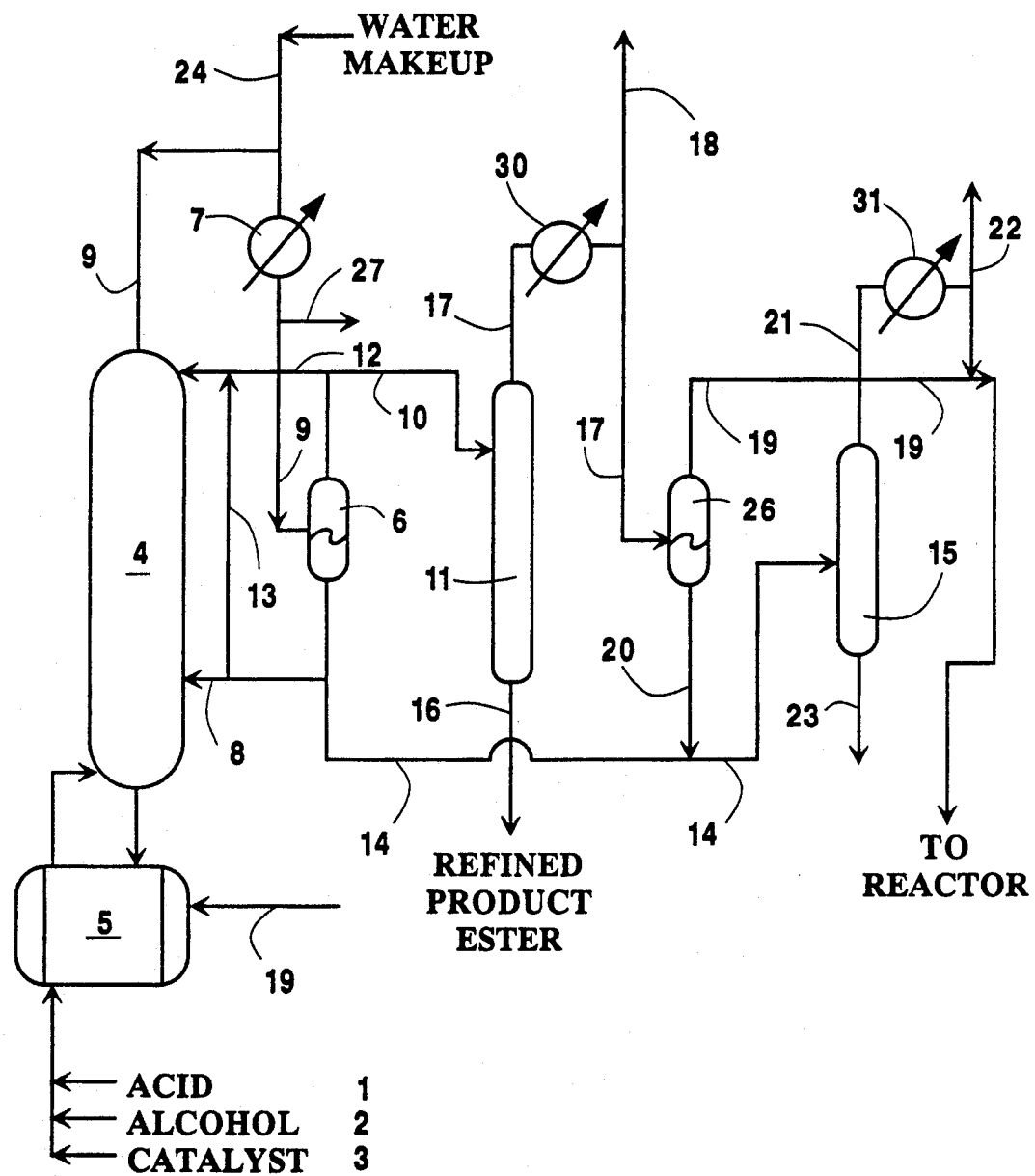

ESTERIFICATION PROCESS

FIELD OF THE INVENTION

This invention relates to an improved process for producing a product ester by the esterification of a lower hydrocarbyl carboxylic acid with an alcohol in the presence of an esterification catalyst, wherein the improvement comprises employing as the catalyst a long chain alkyl substituted benzene sulfonic acid.

BACKGROUND OF THE INVENTION

Methods for producing a product ester by the esterification of a lower hydrocarbyl carboxylic acid with an alcohol in the presence of an esterification catalyst are well known in the art. A preferred conventional process for the manufacture of such product esters comprises esterifying the carboxylic acid and alcohol in a reactor containing a substantially anhydrous reaction medium which also contains the esterification catalyst; obtaining a volatilized product ester-water azeotrope from a distillation column connected to the reaction vessel, and recovering the product ester via phase separation of the product ester-water azeotrope in a separate vessel. For instance, British Patents 1,173,089 and 1,262,645 disclose such a process using sulfuric acid or para-toluene sulfonic acid as the esterification catalyst. Moreover, if desired, a dialkyl sulfate such as dimethyl sulfate or diethyl sulfate may be employed as a catalyst precursor to form an in situ hydrolyzed catalytic equilibrium mixture of monoalkyl sulfate and sulfuric acid. Further European Patent Publication No. 009886 also teaches the use of a strong mineral acid such as sulfuric acid or p-toluene sulfonic acid as the catalyst in such a process, while European Patent Publication No. 158,499 advocates that the catalyst be an alkyl sulfonic acid of the formula $RSO_3H$ wherein R is a $C_1$ to $C_{12}$ substituted or unsubstituted aliphatic hydrocarbyl group with the added proviso that the alkyl sulfonic acid have a desulfonation temperature in excess of 186° C., the preferred catalyst being methanesulfonic acid ($CH_3SO_3H$).

However, it has been found that the presence of acidic sulfate ($SO_4^{-2}$) in the product ester can be highly detrimental to the storage capabilities of such product esters. For instance, the presence of even a fairly moderate amount of acidic sulfate in the product ester has been surprisingly found to be the cause of product ester instability with regard to unacceptable carboxylic acid formation via decomposition of the product ester upon storage. For example a product butyl acetate containing about 0.70 ppm $SO_4^{-2}$ and having an initial carboxylic acidity of about 0.010 percent acetic acid at 24° C., was found to have increased in said acidity to 0.05 percent after days of storage; to 0.125 percent after 43 days and to 0.175 percent after 69 days. Such high amounts of acetic acid obtained upon storage would render the stored product ester unacceptable to the customer.

The acidic sulfate found in the product ester is believed to catalyze hydrolysis of the product ester back to the carboxylic acid and alcohol starting materials thus limiting or shortening the shelf life or storage capability of the product ester. It is further believed that the source of such acidic sulfate in the product esters is derived from thermal decomposition of the corresponding in situ formed sulfonate esters of the acid catalyst employed during the esterification process to sulfur oxides (e.g. $SO_2/SO_3$) which appear in the product as acidic sulfate (i.e., $SO_4^{-2}$). The sulfonate esters are derived from the esterification of the acid catalysts themselves with the alcohol present in the reaction medium. Thus the production of product esters containing as little of such acidic sulfate as possible is very desirable to the product ester manufacturer.

SUMMARY OF THE INVENTION

It has now been discovered that the presence of such acidic sulfate in product esters produced by the above described esterification procedure can be easily minimized by employing as the esterification catalyst, a long chain alkyl substituted benzene sulfonic acid.

Thus it is an object of this invention to provide an improved esterification process for producing such product esters wherein the amount of acidic sulfate in the product ester is minimized by employing a long chain alkyl substituted benzene sulfonic acid as the esterification catalyst, thereby obtaining product esters having excellent storage stability. Other objects and advantages of this invention will become readily apparent from the following written description and appended claims.

Accordingly, a generic aspect of this invention can be described as an improved process for producing a product ester having the formula

RCOOR' wherein R is a hydrocarbyl radical having from 1 to 4 carbon atoms and wherein R' is an alkyl radical having from 2 to 5 carbon atoms, said process consisting essentially of (1) continuously feeding substantially equimolar amounts of carboxylic acid of the formula

RCOOH and an alkanol of the formula

R'OH wherein R and R' are the same as defined above, to a reaction vessel containing a substantially anhydrous reaction medium that contains the carboxylic acid, alkanol, product ester, an esterification catalyst, and not more than about 5 percent by weight water; (2) removing product ester and water from said reaction vessel by distillation to a distillation column; (3) adding water to said distillation column to aid in forming a product ester-water azeotrope; and (4) phase separating said product ester-water azeotrope in a separate vessel to obtain said product ester; the improvement comprising minimizing the amount of acidic sulfate contained in said product ester by employing as said esterification catalyst an alkylbenzene sulfonic acid of the formula

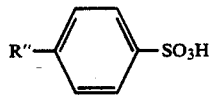

wherein R" is an alkyl radical having from 8 to 20 carbon atoms.

BRIEF DESCRIPTION OF THE DRAWINGS

The drawing schematically illustrates a flow diagram embodiment of the esterification process of this invention, wherein product ester and water are conveyed from the reactor to a distillation column, a product ester-water azeotrope is obtained, the product ester-water azeotrope is then phase separated in a decanter to obtain crude product ester which may be refined if desired.

DESCRIPTION OF THE PREFERRED EMBODIMENTS

Accordingly the subject invention encompasses the carrying out of any known esterification process for producing a product ester, wherein an alcohol containing from 2 to 5 carbon atoms is reacted with a hydrocarbyl carboxylic acid containing from 1 to 4 carbon atoms in the hydrocarbyl radical in a substantially anhydrous reaction medium in the presence of an esterification catalyst, said product ester being recovered via phase separation from a product ester-water azeotrope, the improvement comprising employing the long chain alkyl substituted benzene sulfonic acid catalysts disclosed herein to minimize the formation of undesirable acidic sulfate in the product ester.

Thus the generic reaction conditions and processing techniques of this invention are not narrowly critical and may correspond, if desired and appropriate, to any of the known conditions heretofore employed in such conventional esterification processes. Indeed such reaction conditions and processing techniques may be varied widely and tailored to meet individual needs and produce the particular product ester desired.

For instance, product esters of this invention are those of the formula

RCOOR' wherein R represents a linear hydrocarbyl radical having from 1 to 4 carbon atoms and wherein R' represents an alkyl radical having from 2 to 5 carbon atoms. Illustrative product esters include ethyl acetate, n-propyl acetate, iso-propyl acetate, n-butyl acetate, iso-butyl acetate, amyl acetates, such as n-pentyl acetate, 2-methyl-1-butyl acetate and 3-methyl-1-butyl acetate, ethyl propionate, n-propyl propionate, iso-propyl propionate, n-butyl propionate, iso-butyl propionate, amyl propionates, such as n-pentyl propionate, 2-methyl-1-butyl propionate and 3-methyl-1-butyl propionate, ethyl acrylate, n-propyl acrylate, iso-propyl acrylate, n-butyl acrylate, iso-butyl acrylate, amyl acrylates, n-propyl methacrylate, n-butyl methacrylate, n-butyl butyrate, and the like. The preferred product esters this invention are the propyl and butyl acetates and propionates, the more preferred esters being the acetates, especially n-butyl acetate.

Thus the carboxylic acid starting materials employable in this invention are those of the formula

RCOOH wherein R represents a hydrocarbyl radical having from 1 to 4 carbon atoms. Illustrative carboxylic acids include acetic acid, propionic acid, butanoic acid, isobutanoic acid, acrylic acid and methacrylic acid. The preferred carboxylic acid starting materials are acetic and propionic acid, especially acetic acid. Most preferably the carboxylic acid starting materials are purified single carboxylic acids, although mixtures of such acids could be employed if desired.

The alcohol starting materials employable in this invention are those of the formula

R'OH wherein R' represents an alkyl radical having from 2 to 5 carbon atoms. Illustrative alcohols include ethanol, n-propanol, iso-propanol, n-butanol, iso-butanol, sec-butanol, tert-butanol, amyl alcohols such as 1-pentanol, 2-methyl-1-butanol, 3-methyl-1-butanol, and mixtures thereof, and the like. The preferred alcohols are n-propanol, iso-propanol, n-butanol, and iso-butanol, especially n-butanol. It is of course to be understood that while it is more preferred to employ purified single alcohol starting materials, mixtures of alcohols, preferably those having the same number of carbon atoms, may be employed if desired. For example, amyl alcohol is commonly commercialized in the form of mixed $C_5$ alcohols.

As noted above the esterification catalysts employable in this invention are long chain alkyl benzene sulfonic acids of the formula

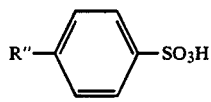

wherein R'' represents an alkyl radical having from 8 to 20 carbon atoms. Such acids as well as methods for their preparation are well known. Of course it is to be understood that as employed herein, said formula is to be considered as encompassing mixtures the individual acid compounds represented by said formula, as well as the individual acid compounds themselves. For example in addition to employing such individual acids per se, it may be more convenient or desirable to employ the commercial or technical grade compounds of such acids (i.e. a mixture of such individual acids where in the alkyl radical shown as R'' is commonly expressed as representing an average number of carbon atoms in the range of from 8 to 20, e.g. those normally used in manufacturing detergents). Thus illustrative alkyl substituted benzene sulfonic acids, include n-octylbenzene sulfonic acid, n-nonylbenzene sulfonic acid, n-decylbenzene sulfonic acid, n-undecylbenzene sulfonic acid, n-dodecylbenzene sulfonic acid, n-tridecylbenzene sulfonic acid, n-tetradecylbenzene sulfonic acid, n-pentadecylbenzene sulfonic acid, n-hexadecyl benzene sulfonic acid, n-heptadecylbenzene sulfonic acid, n-octadecylbenzene sulfonic acid, n-nonyldecyl benzene sulfonic acid, n-eicosylbenzene sulfonic acid, and mixtures thereof. Illustrative commercial grade mixtures of the alkyl benzene sulfonic acids of the above formula available to the Public include Bio-Soft ®S-100 which has an equivalent weight of about 318 and wherein R'' represents an average alkyl chain length of about 11.5 carbon atoms (Stepan Co), AAS-98S a linear alkylbenzene sulfonic acid with an average alkyl chain length of $C_{11}$–$C_{12}$ (Continental Chemical Co.), Vista SA697 and Vista SA 597 a $C_{13}$ linear alkyl benzene sulfonic acid (average mol. wt. 342) and a $C_{11}$ linear alkylbenzene sulfonic acid (average mol wt. 318), respectively, (both products of the Vista Chemical Co.), Stepantan ®H-100 la branched dodecylbenzene sulfonic acid (Stepan Co.), a linear alkyl benzene sulfonic acid wherein the alkyl radical (R'') constitutes about 1% $C_{10}$, 40% $C_{11}$, 28% $C_{12}$ and 31% $C_{13}+$ (Alfa Products Co.), and the like. The more preferred alkylbenzene sulfonic acid catalysts of the above formula are those wherein R" represents an alkyl radical having from 10 to 14 carbon atoms, the most preferred catalyst being the commercial Bio-Soft ® S-100 described above.

The esterification process of this invention is a well known mildly exothermic equilibrium reaction. The basic process can be carried out in a conventional esters batch still kettle reactor wherein product ester and water are removed from the equilibrium esterification reaction as a mixture of binary and ternary heterogeneous azeotropes between the ester, alcohol, and water in a conventional esters batch still distillation column and allowed to phase separate in a decanter. Any suitable conventional esters type reactor and distillation column can be employed herein. However in view of possible acid corrosion problems over time it is preferred to employ corrosion resistant type materials, e.g. 316 stainless steel, of construction for such units. Moreover, it is further preferred that the ester batch still distillation column consist of at least 30 Oldershaw trays or plates the upper number of said trays or plates, being constrained only by practical considerations.

A preferred startup procedure is to begin by adding a conventional feed ratio of substantially equimolar amounts of alcohol and acid to an initially charged reactor. An illustrative initial charge might consist for example of 35-50 wt. % acetic acid, 10-50 wt % butanol, 0-50 wt. % butyl acetate and 0-5 wt. % water. Once the initial charge has been added to the reactor, the esterification catalyst should be added. The reaction contents are then slowly heated and the esters batch still distillation column brought up on total reflux. Equilibrium should be achieved in a very short time (e.g. less than one hour) by this technique.

Another startup procedure is to start near equilibrium condition to enhance the steadiness of the operation. For instance in the case of butyl acetate this may be achieved with an approximate starting composition of 35 wt. % acetic acid, 10 wt. % n-butanol, 50 wt. % butyl acetate and 5 wt. % water followed by addition of the esterification catalyst. When such a steady-state composition is charged to the reactor the esters batch still distillation column can be rapidly line-out to constant conditions in about one-half hour. Additions as desired to the distillation column can be commenced without delay. Such a startup procedure can save time in a plant depending upon the specific conditions such as type of equipment any availability of crude product ester.

As mentioned, once the esters distillation column is brought to total reflux it is allowed to line out to constant conditions. During equilibration the reactor temperature lowers somewhat due to the formation of the product ester and water. Lining out of the reactor and distillation column temperature is a good indication that equilibrium has been achieved.

After equilibrium has been achieved the alcohol and acid are fed continuously to the reactor, preferably in a substantially equimolar ratio. As employed herein the expression substantially equimolar ratio includes molar ratios of alcohol to acid in the range of from about 1 to 1.5:1. Of course such includes equimolar ratios of such reactants and higher or lower alcohol to acid ratios may also be employed if desired. In general it is preferred to employ a slight excess of alcohol to the acid (e.g., about a 1.05:1 molar ratio of n-butanol to acetic acid).

The quantity of esterification catalyst employed in this invention can be any catalytic amount that will advance the reaction rate of the process. However, preferably the catalyst should obviously produce a rapid reaction. This the concentration of the alkyl substituted benzene sulfonic acid esterification catalysts of this invention in reaction medium of the esters batch still reactor may be in the range of about 0.1 to about 5.0 wt. % acidity, calculated as wt. % $H_2SO_4$. Preferably it is maintained in the range of from about 0.1 to to about 2.0 wt. % and more preferably from about 0.2 to about 0.8 wt. % calculated as wt. % $H_2SO_4$. Preferably the catalyst level should remain constant and may be monitored daily by titration. If the acidity level should drop below an acceptable level, makeup catalyst may be added to the reactor to achieve whatever reaction rate is desired.

The esterification process of this invention may be operated at any suitably known reaction temperatures and pressures. For instance, the process described herein may be operated at pressures ranging from atmospheric pressure to about 75 psia, or higher if desired; preferred pressures ranging from atmospheric pressure to about 45 psia. For example in the case of producing butyl acetate it is generally preferred to maintain the reactor and distillation column at a pressure slightly above atmospheric, e.g. 16 to 20 psia. Likewise the esterification reaction may be generically conducted at a temperature ranging from about 80° C. to 180° C. and preferably from about 85° C. to about 140° C. Of course the most preferred reaction conditions in any one individual circumstance will depend to a large extent upon the particular product ester and processing efficiency desired by the operator and such conditions should be readily determinable by one skilled in the art following the more preferred aspects of this invention as explained herein and/or through simple routine experimentation. For example with Bio Soft ® S-100 catalyst it has been found that butyl acetate can be readily obtained at a reactor temperature of about 120° C. and atmospheric pressure while at a pressure slightly above atmospheric pressure (e.g. about 16-20 psia) one can efficiently employ a reactor temperature of about 135° C. Of course it is desirable not to force too high a reaction temperature in order to maintain low overhead carboxylic acid acidity and high crude product ester purities. Most preferably the esterification process of this invention is carried out at steady-state operating conditions so as to promote as much consumption of the alcohol as possible in order to prevent alcohol from entering the distillation column and to prevent it from passing overhead as a low boiling water azeotrope and/or etherifying into a dialkyl ether by-product. Thus it is preferred to monitor the carboxylic acid acidity in the reaction medium e.g. by titration and to maintain said acidity level at a steady state.

The subject esterification process of this invention involves a substantially anhydrous reaction medium, i.e. one containing no more than about 5 wt. % water, in the reactor, and preferably one in which the reaction medium contains less than about 3 wt. % water. Limiting the amount of water in the reactor to such minor amounts permits high react on rates and assures maximum product ester concentration in the reactor. Such low concentrations of water are achievable because while the esterificaton process produces water as a by-product, both the product ester and water formed are readily distilled from the reactor and conveyed to a distillation column wherein aqueous azeotropes are formed, of which water makes up a large percentage (e.g. about 25-30%).

In general it is also preferred to add some water to the distillation column to aid in forming the product ester-water azeotrope, since the amount of water normally distilled from the reactor is not generally sufficient to ensure a satisfactory aqueous azeotrope with the product ester. On the other hand if the water content of the product ester-water azeotrope is too high such is also not desirable. Nor is it desirable to employ too low or high a temperature in the distillation column for removal of the product ester-azeotrope overhead. For example, if the temperature in the distillation column is too high above the boiling point of the product ester-water azeotrope, excessive carboxylic acid may be carried overhead and if said temperature is too low (such as might be caused by excessive water being added to the distillation column) then the crude product ester may be contaminated with excessive alcohol carryover. Thus the temperature in the distillation column, is preferably monitored at any suitable point (e.g. slightly above the lower addition point of water to the distillation column) in the distillation column to control it right at or near the boiling point of the product ester-water azeotrope. The amount of water added to the column is preferably that amount which will achieve the most efficient results in terms of both the amount of product ester obtained and its crude product purity. Moreover, while water is preferably added to a tray close to the bottom of the distillation column to aid in product ester removal from the reactor as an azeotrope, it is also preferred to add some water to a tray at or near the top of the distillation column along with some portion of the crude product ester obtained from the decanter upon phase separation of the product ester-water azeotrope in order to establish a reflux and minimize the amount of carboxylic acid in the crude product taken overhead. Moreover, while it is preferred herein that the water added to the distillation column be derived from the decanter upon phase separation of the product ester-water azeotrope, such need not be the case. The water added to the distillation column may be fresh water if desired, such as from the same fresh water source preferably added to the decanter to aid in the phase separation of the product ester-water azeotrope. In any event water purity can exhibit a significant effect on product quality and productivity. Thus it is preferred that the fresh water source be deionized water or some other high purity type of water. Moreover it is obviously generally preferred to employ sufficient water flow rates, to the upper and lower locations of the distillation column to achieve a highly efficient steady-rate esterification system, e.g., in the case of butyl acetate water flow rates of about 0.5 and 0.3 lbs., respectively, per lb. of butanol feed, may be sufficient.

As noted the addition of some of the crude product ester obtained upon phase separation of the product ester-water azeotrope to the top part of the distillation column is preferred to produce a reflux that aids in keeping carboxylic acid from going overhead and contaminating the product ester. In general it is preferred to return at least a sufficient amount of such crude product ester (along with water) so as to maintain about a 1:1 reflux ratio at the top of the distillation column. Of course higher amounts of product ester can be recycled to obtain higher reflux ratios (e.g. up to 3:1 or more) if desired.

Beneficial factors involved in the employment of the alkyl substituted benzene sulfonic acid catalysts in the esterification process of this invention are many, not the least of which is the production of product esters that are very stable against carboxylic acid formation upon storage as described herein. As noted this stability is considered to be the result of the fact that the long chain alkylbenzene sulfonic acid catalysts of this invention resist formation of unstable sulfonic esters (e.g. from the reaction of an alcohol and the catalyst itself), thus preventing the appearance of acidic sulfate in the product ester and the corresponding carboxylic acid acidity problems on storage of the product. It has also been surprisingly found that the presence of certain neutral acidic sulfate such as that which might be derived from glass apparently does not cause an increase in carboxylic acid acidity upon storage. Indeed it was found that the carboxylic acid acidity of n-butyl acetate did not change with time when stored in a glass container, despite having increased in sulfate content. This increase in sulfate is believed to have been caused by contamination from the glass (typically the sulfate content of small ester samples stored in glass vessels have been found to increase from 1 to 5 ppm). Thus such sulfate originating from the glass is apparently not catalytic in causing hydrolysis of the ester to its carboxylic acid in contrast to that hydrolysis caused by acidic sulfate that originates from reaction of the alcohol and sulfonic acid catalyst itself. In addition to the major advantage of minimizing the amount of acidic sulfate contained in the product ester that is obtainable by employing the subject invention, numerous other advantages may be attributed to the use of the particular alkylbenzene sulfonic acid catalysts of this invention. For example, such very stable catalysts exhibit high catalytic activity and also help provide for a very stable reaction medium in the reactor. Indeed it is considered that the catalysts of the subject invention should greatly minimize the present need for frequent catalyst makeup additions during the esterification process such as commonly required with heretofore conventional catalysts. Moreover it is considered that the long chain alkylbenzene sulfonic acid catalysts of this invention will minimize corrosion problems and also do not appear to cause charring or fouling of the heating coils during esterification. Further due to the excellent stability of the catalyst of this invention, at the completion of a particular product ester production campaign it is considered that the reactor kettle residues containing the used long chain alkylbenzene sulfonic acid catalyst may be readily stripped from the reactor (e.g. when it is desired to start a new production run directed to a different product ester using the same production equipment and facilities), stored and then reused, thus allowing recycling of the catalyst residues from one product ester production campaign to another, when desired. Indeed it is anticipated that reactor kettle residues containing the catalysts of this invention may be recycled 2-3 times before disposal (although some makeup catalyst may be required to restore full activity). In general kettle residues containing heretofore conventional esterification catalysts are not readily reuseable due to variable amounts of char and metals from corrosion contained in the used catalyst composition.

Finally the product esters of the esterification process of this invention have a wide range of utility that is well known and documented. For example esters such as the alkyl acetates and alkyl propionates are especially useful e.g. as solvents in paints and as raw materials for agricultural applications such as insecticides, herbicides, etc.; while esters such as the alkyl acrylates and methacrylates are especially useful as monomers for polymers and resins used in coatings, adhesives and plastics, as well as in textiles and leather finishes and in paints.

Accordingly a preferred embodiment of this invention can be further illustrated by reference to the drawing which schematically shows a diagrammatic flow procedure suitable for practicing this invention.

Shown in said drawing is a reactor (5) (i.e. a conventional esters batch still kettle) to which the carboxylic acid (1) and alcohol (2) may be continuously fed at a temperature sufficient to vaporize the product ester and water to a distillation column (4) (e.g. a conventional ester batch still distillation column). The catalyst (3) (i.e. the alkyl substituted benzene sulfonic acid) is present in the alcohol/carboxylic acid reaction medium of the reactor and make up catalyst may be added incrementally to the esterification reaction if required or desired.

Product ester may be removed from the equilibrium esterification reaction system as a mixture of binary and ternary heterogeneous azeotropes between the ester, alcohol and water from said distillation column (4) via line (9) which is equipped with a cooler or condenser (7). The condensed liquid may then be conveyed to a conventional ester-water azeotrope decanter (6) in which phase separation is allowed to occur. The crude product ester rich top layer of decanter (6) may be fed via lines to a conventional product ester refining still (11) to distill off lights and obtain the desired refined product ester via line (16). A portion of said crude product ester rich top layer of decanter (6) may be returned via line (12) to the top of distillation column (4) to maintain the desired reflux ratio.

The bottom aqueous layer of decanter (6) may be added via lines (8) and (13) to the distillation column (4) in order to satisfy the azeotropic water requirements for product ester removal and to minimize carboxylic acid from distilling overhead with the product ester-water azeotrope mixture via line (9).

Fresh make-up water line (24) may be added to decanter (6) via line (9) to aid in the phase separation and provide sufficient water for distillation column (4). Further line (9) may contain a vent gas line 27, while reactor (5) may be connected to a stripped storage residues tank (not shown) if desired. Excess water may be purged downstream e.g. via line (14).

The lights, e.g., carboxylic acid and alcohol obtained via line (17) from the top of refining still (11) may be reworked by condensing them in cooler (30) and allowing them to phase separate in a second conventional decanter (26) so that the carboxylic acid enriched top layer of said decanter (26) may be recycled via line (19) to reactor (5). Line (17) may contain a vent gas line (18). The bottom layer of said decanter (26) may be conveyed via line (20) to line (14) carrying the water from the first decanter (6) to a final conventional refining or stripping still (15). The vaporized gases e.g. product ester, etc. obtained via line (21) from the top of said stripping still (15) may be condensed via cooler (31) and added to recycle line (19) or discarded via vent gas line (22), as desired. Finally the excess water recovered from the bottom of said stripping still (15) via line (23) can be disposed of as desired in any suitable environmentally correct manner.

The following examples are illustrative of the present invention and are not to be regarded as limitive. It is to be understood that all parts, percentages and proportions referred to herein and in the appended claims are by weight unless otherwise indicated.

SULFATE DETERMINATIONS

The process employed by this invention in determining the amount of acidic sulfate ($SO_4^{-2}$), measured as $Na_2SO_4$, in the process and product ester is by ion chromatography (IC) as follows:

The principal in detecting the acidic sulfate in the water immiscible product ester involves extracting a sample of the product ester with a dilute solution of sodium hydroxide. For example the butyl acetate volume is three times the volume of the dilute base resulting in a three fold concentration of the sulfate in the dilute base layer. The dilute base extract is then injected into an ion chromatograph to measure the sulfate concentration. Recovery of sulfate by this method is 97 to 103 percent.

| INSTRUMENT PARAMETERS | |
|---|---|
| Instrument | Dionex Model 202i, or equivalent |
| Columns | Dionex AG4A and AS4A and AMMS |
| Inline Filter | Dionex Column |
| Temperature | Ambient |
| Detector | Dionex conductivity CDM |
| Mobile Phase | 2.5 mM sodium carbonate and 1.5 mM sodium bicarbonate in H20 |
| Flow | 1.5 mL/min |
| Pressure | 1000 psig |
| Regenerate | 25 mN H2SO4 |
| Flow | 3-4 mL/min |
| Regenerate Press. | 5 psig |
| Conductivity | 16–18μ Siemens background |
| Sample loop | 50μ liters |
| REAGENTS | |
| Water | ASTM type I Water conductivity exceeded 16.7 megohms resistance. The sulfate concentration in the deionized water should be less than 50 ppb as measured by IC. |
| NaOH | 50% liquid high purity low carbonate solution |
| Na2CO3 | ACS Reagent grade (Am. Chem. Soc.) |
| NaHCO3 | ACS Reagent grade (Am. Chem. Soc.) |
| Na2SO4 | ACS Reagent grade (Am. Chem. Soc.) |
| H2SO4 | high purity low metals content |
| 0.01 N NaOH | 50% NaOH, 0.8 g diluted to 1 L. |

STANDARD PREPARATION

Prepare a standard stock solution in water containing approximately 1000 ppm sulfate, as $SO_4^{-2}$, from sodium sulfate. Prepare a second standard containing approximately 1 ppm sulfate in the 0.01N NaOH. Chromatograph the standard along with the samples and blanks.

SAMPLE PREPARATION (E.G., BUTYL ACETATE)

a) Because the levels of sulfate in the samples may be in the parts per billion (ppb) range, contamination should be a constant concern. The samples should be taken and handled in containers that are relatively free of sulfate. Samples and dilutions should be stored in plastic bottles, because glass bottles usually contain several ppm sulfate. To test for sulfate in the containers, add deionized or other high purity water, shake vigorously and analyze the water for sulfate. Regardless of the containers used, blank analyses are essential to correct for sulfate brought in the analysis by the reagents, containers and other sources.

b) Analyze each sample in duplicate. Some process samples may contain two layers. The upper layer is mostly butyl acetate and the bottom layer is mostly water. Either layer can be analyzed for sulfate. The dilute base lower layer of the sample can be analyzed directly or with dilution. The organic part cannot be injected directly into the ion chromatograph (IC) without damaging the columns. Use the extraction procedure in step (c) for the upper butyl acetate layer.

c) Refined butyl acetate samples and the upper layers from unit process samples should be analyzed as follows. Shake thirty, 30±1, grams of each organic sample with ten, 10±, grams of 0.01 NaOH in 50 mL polyethylene plastic bottles. Soon after the layers separate carefully remove some of the bottom dilute base layer and inject into the IC.

d) Repeat in duplicate using the reagents and containers but no sample to provide two blanks for the IC analysis.

e) Samples should be run in random order if possible. The analysis of the samples should be corrected for sulfate found in the 0.01N NaOH blank chromatograms. The 0.01N NaOH will probably contain between 10 and 50 ppb sulfate.

ACIDITY DETERMINATIONS

The process employed by this invention is determining the amount of carboxylic acidity in the process and product ester is as follows.

(a) Introduce 60 mL (60 g) of the sample into a 250 mL Erlenmeyer flask by means of a suitable transfer graduate.

(b) Add a few drops of 1.0 percent alcoholic phenolphthalein indicator and titrate with standard 0.1N alcoholic potassium hydroxide to a pink end point permanent for at least 15 seconds.

(c) Calculation: mL KOH×0.01=acidity, % by weight, e.g., as acetic acid.

CATALYST CONCENTRATIONS DETERMINATIONS

The process employed by this invention in determining the alkyl benzene the acid catalyst concentration in the reaction kettle in terms of sulfuric acid involves tritration with a base. This method actually determines sulfuric acid as the monobasic acid, monobutyl sulfonate, but the results are reported as percent sulfuric acid for convenience. The procedure is as follows:

1. Into each of two 250 mL glass-stoppered flasks pipet 10 mL of sample and add 8 to 10 drops of thymol blue-xylene cyanol FF indicator.

Indicator: 3.0 grams of thymol blue (Na salt from Baxter Scientific Products) and 0.8 grams of xylene cyanol FF (from Fisher, catalog #1131069) dissolved in 1 liter of DMF.

2. Add 100 mL of neutralized anhydrous isopropanol to each of the flasks.

3. Immediately titrate the contents of each flask with standard 0.1N morpholine in isopropanol to a color change from purple to green. Approach the end point dropwise using a 25 mL buret.

4. Calculation:

Sulfuric Acid, % by weight = $A \times N \times 9.81/10 \times Sp.Gv.$

A = ML of N normal morpholine solution required for the sample.

EXAMPLE 1

A continuous process to produce n-butyl acetate was carried out using an esterification system corresponding to the schematic flow diagram of the subject drawing. A 35 Oldershaw tray distillation column was employed.

The esterification reactor kettle was charged with a mixture of n-butanol and acetic acid at a 1:1 molar ratio and 1.0 wt-% of Bio Soft ® S-100 was employed as the esterification catalyst. The reactor contents were heated to 115° to 120° C. while the distillation column and reactor were maintained at about 18–20 psia by pressuring with nitrogen gas. Esterification equilibrium was achieved within 0.5 hours as determined by commencing of n-butyl acetate overhead reflux in the distillation column and by kettle analysis which showed a constant acetic acid content. The catalyst concentration was 0.29 wt. % calculated as sulfuric acid.

An esterification feed mixture of acetic acid and n-butanol in a molar ratio of about 1.00:1.05 was fed continuously to the reactor kettle at a temperature of 110° to 120° C. at 18–20 psia which was sufficient to vaporize the product ester/water azeotrope while maintaining kettle equilibrium. The kettle composition remained essentially constant during the process, while the catalyst concentration ranged from 0.29% to 0.32% calculated as sulfuric acid (the slight variation was due to variation in kettle liquid level).

The product ester left the top of the distillation column, as a mixture of binary and ternary heterogeneous azeotropes between n-butyl acetate, n-butanol and water, and was allowed to phase separate into product ester-rich upper and a water-rich lower layers in a decanter, after passing through a cooler. The average composition of the decanter lower water layer was found to contain 300 ppb (0.30 ppm) of acidic sulfate.

About one-half of the crude product ester upper phase recovered from the decanter was conveyed to a refining still, while the other half of said crude product ester was added back at the head of the distillation column to maintain about a 1:1 reflux.

In this process run, about 1.1 to 1.6 lb. of water per lb. of n-butanol was continuously fed to the top of the distillation column and about 0.9 to 1.1 lb. of water per lb. of n-butanol was added to the lower water feed point (tray 17) of the column. The water layer recovered from the decanter was not recycled to distillation column, but instead fed to a water stripping column for recovery of n-butyl acetate and unreacted butanol and acetic acid, which were returned to the reactor. Purification of the water made it suitable for disposal.

The average acidic sulfate content of the refined n-butyl acetate recovered from refining still and produced by this process run was 20 ppb and the acetic acid acidity was 0.009 wt-%. After standing at 42° C. (107.6° F.) for 23 days, the acetic acid acidity of the refined n-butyl acetate was still found to be 0.009 wt-%, and after 49, 78 and 119 days at 42° C., said acidity was 0.011 wt-%, 0.016 wt. % and 0.015 wt-%, respectively, showing that the obtained n-butyl acetate product ester was very stable against acetic acid formation upon storage.

EXAMPLE 2

A continuous process to produce n-butyl acetate was carried out using an esterification system corresponding to the schematic flow diagram of the subject drawing. A 43 Oldershaw tray distillation column was employed.

The reactor kettle was initially charged with acetic acid followed by Bio-Soft ® S-100 as the esterification catalyst and finally with n-butanol (about a 1.3:1.0 molar ratio of acetic acid to n-butanol) and heating commenced. The amount of catalyst added calculated to be about 1.1 wt-%, while the catalyst content in the reactor was 0.37% calculated as sulfuric acid. Additional acetic acid and butanol were added at 1:1 molar ratio to obtain the desired kettle level.

Heating the reactor was commenced while the distillation column and reactor were maintained at about 30 psia by pressuring with nitrogen gas. After heating 1.5 hours, a reactor temperature of 105° C. had been reached and esterification equilibrium achieved as determined by commencing of n-butyl acetate overhead reflux in the distillation column and a constant acetic acid concentration in the reactor.

An esterification feed mixture of acetic acid and n-butanol in a molar ratio of about 1.00:1.05 was fed continuously while maintaining the reactor temperature at about 125° to 135° C. at 19–22 psia. Water addition was simultaneously commenced to the distillation column in sufficient quantity to form the ester/water azeotrope while maintaining reactor equilibrium throughout the process. The average catalyst concentration during the process was 0.3 wt-% calculated as $H_2SO_4$. The catalyst neither exhibited loss by decomposition nor required makeup additions during this process which was run continuously for several weeks.

The overhead product ester-water azeotrope leaving the column was condensed by a cooler and phase separated in a decanter vessel. The average acidic sulfate content of the crude n-butyl acetate rich top layer stream was determined to be 25 ppb. The average acidic sulfate content of the decanter lower water layer was 300 ppb.

Some of the upper product ester-rich layer from the decanter was fed to refining still to produce refined n-butylacetate product and the remainder was returned to the head of the distillation column to maintain about a 1:1 reflux.

About 1.6 lb to 1.8 lb of the decanter water phase per lb of n-butanol fed to the system was returned to the head of the distillation column, and about 0.40 lb to 0.65 lb of the decanter water layer per lb of n-butanol was fed to the lower point (tray 4) on the distillation column. The remaining water from the decanter was fed to a water stripping column for recovery of n-butyl acetate and unreacted butanol and acetic acid, which were returned to the reactor. Purification of the water made it suitable for disposal.

Sufficient fresh water was added to the decanter to maintain a sharp liquid level in the decanter and provide for the water added to distillation column.

The average acidic sulfate content of the refined n-butyl acetate produced by this process run was 25 ppb and the average acetic acid acidity was 0.006 wt-%.

EXAMPLE 3

The following experimental data in Table I, illustrates the reactive consumption of various acid catalysts, i.e. methane sulfonic acid (MSA), p-toluene sulfonic acid (p-TSA), sulfuric acid ($H_2SO_4$), Bio-Soft ® S-100 (referred to in this example as dodecylbenzene sulfonic acid or DBSA) and p-octylbenzene sulfonic acid (OBSA) with n-butanol at 115° C. with regard to forming sulfonate ester.

TABLE I

| MSA | | p TSA | | $H_2SO_4$ | | DBSA | | OBSA | |
|---|---|---|---|---|---|---|---|---|---|
| Time Hrs. | Wt. % Acid Reacted | Time Hrs. | Wt. % Acid Reacted | Time Hrs. | Wt. % Acid Reacted | Time Hrs. | Wt. % Acid Reacted | Time Hrs. | Wt. % Acid Reacted |
| 1.0 | 00.00 | 4.00 | 00.00 | 4.00 | 100.00 | 7.00 | 1.84 | 7 | 2.85 |
| 7.0 | 11.11 | 13.00 | 21.85 | 11.50 | 96.78 | 12.50 | 4.79 | 13 | 2.31 |
| 13.0 | 22.22 | 20.00 | 24.65 | 19.00 | 98.95 | 13.50 | 0.00 | 21 | 1.76 |
| 20.0 | 20.94 | 27.00 | 21.85 | 36.00 | 99.52 | 21.00 | 2.58 | 29 | 1.49 |
| 28.0 | 22.22 | 40.50 | 15.41 | 59.00 | 99.59 | 28.50 | 1.11 | 39 | 0.68 |
| 42.0 | 29.05 | 48.00 | 16.25 | 85.80 | 92.41 | 34.50 | 0.00 | 61 | 1.22 |
| 49.50 | 27.35 | 88.00 | 21.01 | 92.50 | 88.22 | 41.00 | 0.00 | 92 | 1.76 |
| 72.00 | 20.09 | | | 97.50 | 85.53 | 49.50 | 0.00 | | |
| 89.50 | 19.23 | | | 105.00 | 88.03 | 71.00 | 0.00 | | |
| | | | | 112.00 | 92.05 | 94.50 | 0.00 | | |
| | | | | 121.00 | 84.12 | | | | |

The above data shows that p-TSA and MSA reacted with n-butanol (to the extent of 20–25% in less than 25 hours) forming the corresponding sulfonate esters (butyl p-toluene sulfonate and butyl methane sulfonate respectively). Continued heating at 115° C. up to about 88 hours showed no further reaction suggesting equilibrium had been achieved under the reaction conditions. The data also shows that mixing $H_2SO_4$ and n-butanol formed mono-n-butylsulfate virtually instantaneously (within 30 seconds at 110° C.). In contrast the DBSA catalyst showed little or no reaction with the n-butanol even after heating at 115° C. for over 90 hours, while only a slight degree of esterification to the sulfonate ester was observed for the OBSA catalyst over 90 hours at 115° C. Such data indicates that the long chain alkylbenzene sulfonic acid catalysts of this invention should be much more resistant than other esterification catalysts to the formation of those unstable sulfonic esters that can occur during the acid-alcohol esterification because of reaction between the alcohol and catalyst itself. Moreover, such undesirable sulfonic ester by-products are readily decomposable to sulfur oxides during esterification and are considered to be the root cause of carboxylic acid formation upon storage of product esters.

EXAMPLE 4

In a laboratory-scale glass esterification system corresponding to that used in Example 2, five different catalyst were tested for comparable acidic sulfate generation in the crude product ester. The five catalyst were:

| Catalyst | Example |
|---|---|
| Diethyl Sulfate | A |
| Sulfuric Acid | B |

-continued

| Catalyst | Example |
|---|---|
| p-Toluenesulfonic Acid | C |
| Bio-Soft ® S-100 | D |
| 1-Decanesulfonic Acid | E |

The esterification processes were conducted under typical raw material feed rates to provide comparable distillation column and kettle operation temperatures. The feed ratio rates employed and temperatures observed during a 6 hour run for each experiment were as follows:

| | EXAMPLE | |
|---|---|---|
| | A to C | D to E |
| n-Butanol to Acetic Acid, molar ratio | 1:1.05 | 1:1.05 |
| n-Butanol feed rate, g/hr | 54.4 | 81.6 |
| Acetic Acid feed rate, g/hr | 42.0 | 63.0 |
| H₂O to Top of Column (g/g n-butanol) | 0.50 | 0.33 |
| H₂O to Low Part of Column (g/g n-butanol) | 0.28 | 0.18 |
| H₂O to decanter (g/g n-butanol) | 0.39 | 0.26 |
| Kettle Temp., °C. | 116 | 120-122 |
| Overhead Column Temp., °C. | 90.3-90.4 | 90.3-90.8 |
| Column Control Temp., °C. | 92.0-92.1 | 92.8-100.5 |

Appropriate catalyst concentrations were employed to provide comparable esterification rates. The kettle catalyst concentrations (as % of $H_2SO_4$) and results observed for the various crude product ester compositions of the product ester-rich top layer of the decanter and the acidic sulfate content found in both the product ester-rich top layer and the bottom water-rich layer of the decanter, were as follows:

| | Example | | | | |
|---|---|---|---|---|---|
| | A | B | C | D | E |
| Kettle H₂SO₄, % | 0.30 | 0.37 | 0.15 | 0.21 | 0.18 |
| Kettle Acidity, as Acetic Acid, % | 26.0 | 28.5 | 25.8 | 32.5 | 34.5 |
| Kettle H₂O, % | 1.65 | 1.38 | 1.48 | 2.05 | 0.49 |
| n-Butyl Acetate, top layer, % | 97.02 | 97.64 | 97.03 | 98.81 | 98.03 |
| N-Butanol, top layer, % | 2.20 | 2.33 | 2.49 | 1.12 | 1.43 |
| Acidity, top layer, % | 0.001 | 0.001 | 0.001 | 0.001 | 0.001 |
| H₂O in top layer, % | 1.28 | 1.00 | 1.15 | 1.06 | 0.68 |
| n-Butyl Acetate, ave., mL/hr | 93.3 | 89.2 | 88.3 | 107.5 | 98.3 |
| H₂O Collected, ave., mL/hr | 62.5 | 67.5 | 65.8 | 74.2 | 80 |
| Sulfate in top layer, ppb | 80 | 83 | 78 | 53 | 98 |
| Sulfate in bottom layer, ppb | 220 | 169 | 149 | 80 | 205 |

From the above data and, in particular, from the determined acidic sulfate content in both the top product ester-rich decanter layer and the bottom water-rich decanter layer in each experiment, it is clear that catalyst "D", the long chain alkylbenzene sulfonic acid catalyst, i.e., Bio-Soft ® S-100 of this invention was comparatively far superior in minimizing the amount of acidic sulfate contained in said crude product ester and separated aqueous layer, than that achieved when using such catalysts as sulfuric acid (B), p-toluene sulfonic acid (C), 1-decanesulfonic acid (E) and diethyl sulfate (A).

EXAMPLE 5

A continuous esterification process was carried out using the esterification system and general procedure described in Example 1. In this production run propionic acid was esterified with n-butanol to produce n-butyl propionate.

The reactor was charged with a mixture of n-butanol and propionic acid to give a 25% excess of propionic acid on a molar basis. The acid was added first followed by the n-butanol. During addition of butanol, Bio-Soft ® S-100 (0.88 wt. %) was added to the reactor.

The kettle contents were heated to 105° C. at 18-20 psia and n-butanol and propionic acid fed at 1.05:1.00 molar ratio, respectively. Water addition to the distillation column was commenced after the reactor had been charged and the reaction temperature achieved.

The reaction kettle achieved equilibrium within about two hours. Analysis showed a high equilibrium ester content in the reactor. The lack of di-n-butyl ether in the reaction medium showed the high catalyst selectivity.

The esterification was carried out at an average kettle temperature of 105°-110° C. and a distillation column overhead temperature of about 97° C. Sufficient fresh water (not decanter water) was added to the top and bottom of the distillation column to obtain the desired product ester-water azeotrope.

The product ester-water azeotrope obtained from the distillation column overhead was phase separated in a decanter.

After refining the crude product ester top layer, n-butyl propionate was obtained having a purity in excess of 99.5% The average acidic sulfate content of the refined n-butyl propionate was found to be 26 ppb and the acetic acid acidity was 0.010 wt. %. After standing at 42° C. for 41 and 96 days, said acidity was found to be 0.007 wt. % and 0.019 wt. %, respectively.

EXAMPLE 6 n-Propyl acetate was prepared from reaction of acetic acid with n-propanol in the presence of Bio-Soft ® S-100 catalyst. The esterification system and general procedure described in Example 2 were employed.

The reactor was first filled with acetic acid followed by addition of n-propanol (1.3:1.0 molar ratio of acidic acid to n-propanol). While adding the alcohol Bio-Soft ® S-100 catalyst (2.6 wt. %) was introduced into the reactor. The kettle contents were heated to 120° C., which gave reflux in the distillation column. Additional acetic acid and n-propanol in a 1:1 molar ratio was introduced into the reactor kettle to obtain the desired liquid level. Analysis of the kettle at this point gave an acid catalyst concentration of 0.683%, calculated as $H_2SO_4$.

Heating was continued while water addition to the lower distillation column side and top distillation column trays was initiated. At about this time the column was taken off full reflux and some overhead azeotrope flow was permitted into the decanter. Water flows to the distillation column were stabilized at about 0.03 lb and 0.25 lb per lb of n-propanol feed at the upper and lower feed points on the column, respectively.

The esterification achieved stable operation at a reactor temperature of 120° C. and at distillation column tail and head pressures of 24 and 21 psia respectively.

The catalyst concentration in the reactor was constant at an average of 0.55% acidity as $H_2SO_4$ and did not require additional catalyst, which attests to a high degree of catalyst stability.

The product ester-water azeotrope obtained overhead from the distillation column was condensed in a decanter to obtain a crude n-propyl acetate rich upper phase layer and an aqueous bottom layer phase.

Various modifications and variations of this invention will be obvious to a worker skilled in the art and it is to be understood that such modifications and variations are within the purview of this application and the spirit and scope of the appended claims.

What is claimed is:

1. An improved process for producing a product ester having the formula

RCOOR' wherein R is a linear hydrocarbyl radical having from 1 to 4 carbon atoms and wherein R' is an alkyl radical having from 2 to 5 carbon atoms, with the proviso that said product ester is not an acrylate or a methacrylate, said process consisting essentially of (1) continuously feeding substantially equimolar amounts of carboxylic acid of the formula

RCOOH and an alkanol of the formula

R'OH wherein R and R' are the same as defined above, to a reaction vessel containing a substantially anhydrous reaction medium that contains the carboxylic acid, alkanol, product ester, an esterification catalyst, and not more than about 5 percent by weight water; (2) removing product ester and water from said reaction vessel by distillation to a distillation column; (3) adding water to said distillation column to aid in forming a product ester-water azeotrope; and (4) phase separating said product ester-water azeotrope in a separate vessel to obtain said product ester; the improvement comprising minimizing the amount of acidic sulfate contained in said product ester by employing as said esterification catalyst an alkylbenzene sulfonic acid of the formula

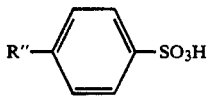

wherein R" is an alkyl radical having from 8 to 20 carbon atoms.

2. A process as defined in claim 1, wherein the esterification catalyst comprises a mixture of individual alkylbenzene sulfonic acids represented by the formula in claim 1.

3. A process as defined in claim 1, wherein R" is an alkyl radical having from 10 to 14 carbon atoms.

4. A process as defined in claim 1, wherein the alcohol is propanol or butanol.

5. A process as defined in claim 4, wherein the carboxylic acid is acetic acid.

6. A process as defined in claim 4, wherein the carboxylic acid is propionic acid.

7. A process as defined in claim 4, wherein the alcohol is n-butanol and the carboxylic acid is acetic acid.

8. A process as defined in claim 4, wherein the alcohol is n-butanol and the carboxylic acid is propionic acid.

9. A process as defined in claim 2, wherein the mixture of said alkylbenzene sulfonic acids is one in which R" represents an alkyl radical having an average of about 11.5 carbon atoms.

10. A process as defined in claim 11, wherein the alcohol is n-butanol and the carboxylic acid is acetic acid.

11. A process as defined in claim 1, wherein the alkylbenzene sulfonic acid catalyst is dodecylbenzene sulfonic acid.

12. A process as defined in claim 1, wherein the water added to the distillation column is derived from the phase separation of the product ester-water azeotrope, and wherein a portion of the product ester of said phase separation is recycled to the distillation column.

13. A process as defined in claim 12, wherein the esterification catalyst comprises a mixture of individual alkylbenzene sulfonic acids represented by the formula

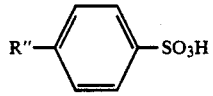

wherein R" is an alkyl radical having from 8 to 20 carbon atoms.

14. A process as defined in claim 12, wherein R" is an alkyl radical having from 10 to 14 carbon atoms.

15. A process as defined in claim 12, wherein the alcohol is propanol or butanol.

16. A process as defined in claim 15, wherein the carboxylic acid is acetic acid.

17. A process as defined in claim 15, wherein the carboxylic acid is propionic acid.

18. A process as defined in claim 15, wherein the alcohol is n-butanol and the carboxylic acid is acetic acid.

19. A process as defined in claim 15, wherein the alcohol is n-butanol and the carboxylic acid is propionic acid.

20. A process as defined in claim 13, wherein the mixture of said alkylbenzene sulfonic acids is one in which R" represents an alkyl radical having an average of about 11.5 carbon atoms.

21. A process as defined in claim 12, wherein the alcohol is n-butanol and the carboxylic acid is acetic acid.

22. A process as defined in claim 12, wherein the alkylbenzene sulfonic acid catalyst is dodecylbenzene sulfonic acid.

* * * * *